United States Patent [19]

Chiang et al.

[11] Patent Number: 5,107,057
[45] Date of Patent: Apr. 21, 1992

[54] CYANO-DIENES, HALOPYRIDINES, INTERMEDIATES AND A PROCESS FOR THEIR PREPARATION

[75] Inventors: George C. Chiang, Wilmington, Del.; Felix E. Granchelli, Arlington; Christopher Wright, Somerville, both of Mass.

[73] Assignee: E. I. Du Pont de Nemours and Company, Wilmington, Del.

[21] Appl. No.: 659,413

[22] PCT Filed: Jan. 3, 1989

[86] PCT No.: PCT/US89/00001
§ 371 Date: Jun. 12, 1990
§ 102(e) Date: Jun. 12, 1990

[87] PCT Pub. No.: WO89/06230
PCT Pub. Date: Jul. 13, 1989

Related U.S. Application Data

[63] Continuation-in-part of Ser. No. 232,535, Aug. 16, 1988, abandoned, which is a continuation of Ser. No. 140,673, Jan. 4, 1988, abandoned.

[51] Int. Cl.$^5$ .................. C07D 213/12; C07D 213/56; C07D 213/62; C07C 255/07
[52] U.S. Cl. .................................. 546/250; 546/294; 546/316; 546/317
[58] Field of Search ............... 546/250, 294, 316, 317; 558/437, 445

[56] References Cited

PUBLICATIONS

Chemical Abstracts, vol. 87, No. 13, Abst. No. 102,266e, Sep. 26, 1977.
Chemical Abstracts, vol. 108, No. 9, Abst. No. 75,417y, Feb. 29, 1988.

Primary Examiner—Alan L. Rotman

[57] ABSTRACT

This invention relates to certain cyano-dienes and halopyridines and the processes for their preparation from a protected 1,3-dialdehyde and a cyano-diene.

9 Claims, No Drawings

CYANO-DIENES, HALOPYRIDINES, INTERMEDIATES AND A PROCESS FOR THEIR PREPARATION

RELATED APPLICATION

This application is a continuation-in-part of copending application U.S. Ser. No. 232,535 filed Aug. 16, 1988 which is a continuation of application U.S. Ser. No. 140,673 filed Jan. 4, 1988, both abandoned

BACKGROUND OF THE INVENTION

This invention relates to certain cyano-dienes and halopyridines and the processes for their preparation from a protected 1,3-dialdehyde and a cyano-diene.

The "sulfonylurea" herbicides are an extremely potent class of herbicides discovered within the last few years which generally consist of a sulfonylurea bridge, —$SO_2NHCONH$—, linking two aromatic or heteroaromatic rings. Research directed to methods for preparing sulfonylurea herbicides is continually producing new processes. The search for improved methods for more effectively preparing such compounds and intermediates required for preparing such compounds continues.

South African Patent Application 870,436 filed Jan. 21, 1987 discloses the use of compounds of Formula I in the preparation of pyridine sulfonylureas.

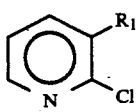

EP-A-237,292 published Sep. 16, 1987 discloses the use of compounds of the above Formula I in the preparation of pyridine sulfonylureas.

J. Org. Chem. 41, 2066 (1976) discloses the preparation of 2-bromonicotinic esters according to the following procedure.

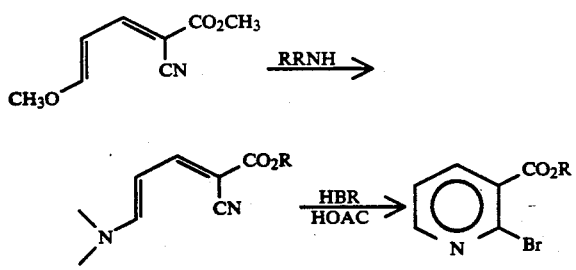

J. Org. Chem. 38, 3436 (1974) discloses the preparation of nicotinamide from the 2-bromonicotinic esters according to the following procedure.

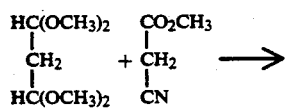

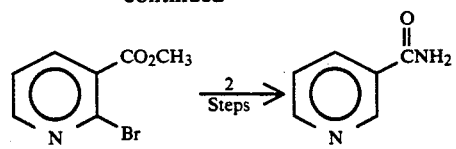

Japanese Patent 80-76,863, priority date Dec. 6, 1978, discloses the preparation of 2-chloro- nicotinic acids according to the following procedure.

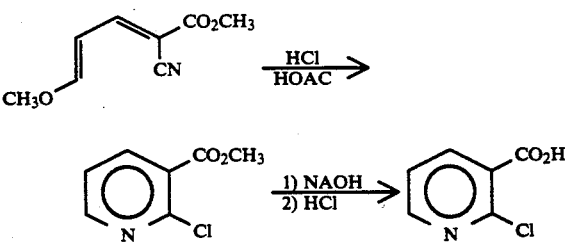

SUMMARY OF THE INVENTION

A process for making intermediates useful for the preparation of herbicidally active sulfonylureas has been discovered as well as novel intermediate compounds. In accordance with the invention, the process for preparing a compound of formula I and its corresponding salts,

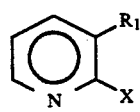

wherein
$R_1$ is $COR_2$ or $SO_2CH_2CH_3$;
$R_2$ is $C_1$-$C_3$ alkyl or $C_1$-$C_2$ dialkylamino; and
X is F, Cl or Br;
comprises reacting a compound of the Formula II with a compound of Formula III

```
CH(OR)2      R1
|            |
CH2          CH2
|            |
CH(OR)2      CN
  II          III
``` wherein R is —$CH_3$ or —$CH_2CH_3$ and $R_1$ is as defined above; in the presence of acetic anhydride, a $ZnX_2$ catalyst where X is as defined above and optionally acetic acid at a temperature of 110° to 150° C. to form a compound of the formula

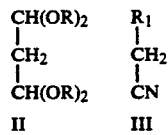

wherein $R_1$ and R are as defined above; and reacting in the presence of acetic acid at a temperature of 0° to 60° C. the compound of Formula IV with HX where X is as defined above.

The compounds of Formula IV

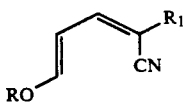

wherein R and $R_1$ are as defined; prepared by the process of the invention are novel and useful for preparing intermediates for the preparation of sulfonylurea herbicides.

Compounds of the Formula I

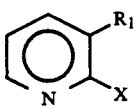

wherein
$R_1$ and X are defined as above;
provided that when R is $C_1$-$C_2$ dialkylamino;
then X is F or Br.
and their corresponding salts prepared by the process of the invention are novel and useful compounds for the preparation of sulfonylurea herbicides.

Preferred for reasons of ease of synthesis and efficiency are:

1. The process of the invention wherein $R_1$ is $C(O)R_2$.
2. The process of Preferred 1 wherein $R_2$ is $C_1$-$C_2$ dialkylamino.
3. The process of the invention wherein $R_1$ is $SO_2CH_2CH_3$.
4. The process of the invention wherein X is Br.
5. The process of the invention wherein the corresponding salt of Formula I is the HBr salt.

The compounds of the invention preferred for their efficiency and ease of synthesis are:

6. The compounds of Formula IV wherein $R_1$ is $C(O)R_2$.
7. The compounds of Preferred 6 wherein $R_2$ is $C_1$-$C_2$ dialkylamino.
8. The compounds of Formula IV wherein $R_1$ is $SO_2CH_2CH_3$.
9. The compounds of Formula I wherein $R_1$ is $CON(CH_3)_2$ and X is F or Br.
10. The compounds of Formula I wherein $R_1$ is $SO_2CH_2CH_3$.
11. The corresponding HBr salt of compounds of Preferred 9.
12. The corresponding HBr salt of compounds of Preferred 10.

The process of the invention can generally be carried out by reacting 1.0 to 3 moles of Compound II, preferably 1.2 to 1.5 moles, per mole of Compound III in the presence of with 1-5 moles of acetic anhydride, preferably 1.5-2.5 moles. Acetic acid can be advantageously used but is not required. Lower temperatures can be used with acetic acid. $ZnX_2$, the catalyst, can be used in amounts of 0.5-2% by weight based on Compound II. The temperature for the reaction may be generally 110°-150° C., preferably 120°-130° C.: the yield of Compound II will vary depending on the condition but yields of 85-90% are achievable.

The second step for the process involving the reaction of Compound IV with HX can generally be carried out with 0.5-8 moles of HX, preferably 2-4 moles of HX. The amount of acetic acid required is generally from 0.2 to 1 liter per mole of reactant, preferably 0.4 to 0.6 liter. The temperature may range from 0°-60° C., preferably 10°-30° C.

By $C_1$-$C_2$ dialkylamino is meant dimethylamino and diethylamino.

DETAILED DESCRIPTION OF THE INVENTION

More specifically, the process of this invention may be carried out by reacting 1.2 to 1.5 moles of a malonodialdehyde bis(acetal) with one mole of a substituted acetonitrile and 1-5 moles of acetic anhydride in acetic acid containing 0.5-2% of a catalytic amount of zinc chloride or zinc bromide. Alternatively, the reaction can be carried out in the absence of acetic acid. The reaction mixture is heated to 110°-150° C. and then distilled overhead until analysis of the pot contents shows a disappearance of starting materials and the formation of Compound IV, which is a mixture of geometric isomers. Compound IV can be isolated by distillation or crystallization. In the next step, it is treated with 0.5 to 8 equivalents of HF, HCl or HBr in acetic acid (200–1000ml/mole) at 0°-60° C. to undergo the cyclization reaction to yield Compound I. Alternatively, Compound IV can be directly cyclized to Compound I without isolation. To help facilitate the isolation of Compound I, excess acid such as HBr may be added to the reaction mixture. The resulting crystalline salt of Compound I can then be separated from the reaction mixture by such means as filtration. The salt of Compound I can be used directly in the preparation of sulfonylurea herbicides. The salt of Compound I can also be neutralized with base to liberate Compound I.

The following Examples further illustrate the invention:

EXAMPLE 1

Preparation of 2-cyano-5-methoxy-N,N-dimethyl-2,4-pentadienamide

To a 250 ml 3-necked R.B. flask was charged 50 g malonodialdehyde bis(dimethylacetal), 22.5 g N,N-dimethyl-2-cyanoacetamide, 60 g acetic anhydride, 0.5 g zinc chloride and 100 ml acetic acid. It was heated to reflux to distill off low boilers until the pot temperature reached 125° C. and head reached 110° C. and a total of 60 ml distillate was collected. GC analysis of the pot content showed disappearance of N,N-dimethyl-2-cyanoacetamide. The reaction mixture was filtered to remove zinc catalyst and then rotovapped. The pot residue was crystallized from a methanol in dry ice-acetone bath to afford 16 g (44.3%) of the title compound.
NMR(DMSO-d6): 2.95 (6H,s), 3.80 (3H,s), 6.85 (1H, t), 7.65 (1H, dd), m/e=180 (theoretical 180)

EXAMPLE 2

Preparation of 2-chloro-N,N-dimethyl-3-pyridine-pentadienamide

To a 250 ml 3-necked R.B. flask was charged 16 g of Compound IV from Example 1 and 150 ml acetic acid. At ambient temperature, 15 g gaseous HCl was fed into the mixture over 20 minutes. The resulting solution was allowed to stand overnight and was then rotovapped. The residue was diluted with 500 ml water and extracted 3 times with 500 ml chloroform. The combined chloroform was dried with anhydrous $MgSO_4$, filtered, rotovapped and then distilled to produce 5.5 g (30%) of the title compound which was identical to an authentic sample by GC, NMR and MS.

EXAMPLE 3

Preparation of
2-chloro-N,N-dimethyl-3-pyridine-carboxamide
(without isolating the intermediate)

To a 250 ml 3-necked flask was charged 40 g malonodialdehyde bis(dimethylacetal), 22.5 g N,N-dimethyl-2-cyanoacetamide, 60 g acetic anhydride, 0.5 g zinc chloride and 100 ml acetic acid. The mixture was heated to reflux to distill off 60 ml of byproducts and then cooled to ambient temperature. The mixture was diluted with 100 ml acetic acid, charged with 60 g gaseous HCl and was allowed to stand overnight. It was rotovapped to remove all solvents and then diluted with water and extracted 3 times with 500 ml chloroform. After drying the chloroform solution with anhydrous MgSO$_4$ and filtering, the filtrate was rotovapped to afford 14.5 g (39%) of the title compound which was identical to an authentic sample by GC, NMR$_1$ and MS.

EXAMPLE 4

Preparation of 2-Bromo-3-(ethylsulfonyl)pyridine

A mixture of 12.3 g (0.075 mole) malonodialdehyde bis(dimethylacetal), 25 ml (0.25 mole) acetic anhydride, and 0.08 g zinc chloride was treated at 91° C. for 25 minutes. Cyanomethyl ethylsulfone (6.7 g, 0.050 mole) was added and the mixture was heated at reflux (95°-109° C.) for 16 hours.

The reaction mixture was cooled to 16° C., and 10 ml of 30% hydrobromic acid in acetic acid was added. An additional 6.5 g of hydrogen bromide gas was added at 15°-20° C. After one hour, the reaction was quenched with 100 ml of ice water. After neutralizing with sodium hydroxide, the mass was extracted twice with methylene chloride, washed with water, dried with magnesium sulfate, filtered, and the solvent evaporated to leave 7.2 g of an oil.

H-NMR$_1$ (CDCl$_3$): δ=8.58 (m, 1H); 8.45 (m, 1H); 7.53 (m, 1H); 3.55 (q, 1H); 1.30 (t, 2H, J=0.04).

A sample prepared similarly and recrystallized from ethyl acetate melted at 78°-79° C.

Elemental analysis calc. for C$_7$H$_8$BrNO$_2$S.
Calculated: C, 33.61; H, 3.22; Br, 31.95; N, 5.60; S, 12.82.
Found: C, 33.87; H, 3.27; Br, 32.60; N, 5.64; S, 12.83.

EXAMPLE 5

Preparation of
2-(ethylsulfonyl)-5-methoxy-2,4-pentadienitrile

A mixture of 57 g (.342 mole) malonodialdehyde bis(dimethylacetal), 95 ml (1.0 mole) acetic anhydride, and 0.5 g of zinc chloride was heated to 95° C. After heating at 90°-95° C., while allowing the methylacetate to distill off for 20 minutes, 33.2 g (0.25 mole) of cyanomethyl ethylsulfone was added. The reaction mass was heated to 120° C. while distilling off further amounts of methylacetate. The reaction was held at 120° C. for 4 hours and then cooled to 25 ° C. Water, 200 ml, was added, then the mass was extracted twice with 200 ml each of methylene chloride. The combined methylene chloride extracts were washed with 10% sodium carbonate and then with water. After drying with anhydrous magnesium sulfate and filtering, the filtrate was evaporated to yield 63.6 g of the desired product. The crude product was recrystallized from chlorobutane to yield yellow crystals, m.p. 72°-74° C.

Elemental analysis calc. for C$_8$H$_{11}$NO$_3$S.
Calculated: C, 47.74; H, 5.51; N, 6.91; S, 15.94.
Found: C, 47.83; H, 5.39; N, 7.18; S, 16.14.
H-NMR$_1$ (CDCl$_3$): δ=7.70 (d, 1H); 7.38 (d, 1H); 6.04-5.98 (dd, 1H); 3.91 (s, 3H); 3.21 (q, 2H); 1.38 (t, 3H).

The following entries in Tables I and II may be prepared using the methods taught in the above examples.

TABLE I

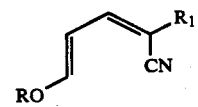

| R | R$_1$ | Physical Data |
|---|---|---|
| CH$_3$ | CON(CH$_3$)$_2$ | NMR δ 2.95 (6H, s) |
| CH$_3$ | CON(CH$_2$CH$_3$)CH$_3$ | |
| CH$_3$ | CON(CH$_2$CH$_3$)$_2$ | |
| CH$_3$ | SO$_2$CH$_2$CH$_3$ | m.p. 72-74° C. |
| CH$_2$CH$_3$ | CON(CH$_3$)$_2$ | |
| CH$_2$CH$_3$ | CON(CH$_3$)CH$_2$CH$_3$ | |
| CH$_2$CH$_3$ | CON(CH$_2$CH$_3$)$_2$ | |
| CH$_2$CH$_3$ | SO$_2$CH$_2$CH$_3$ | |

TABLE II

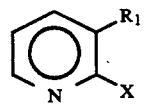

| R$_1$ | X | Physical Data |
|---|---|---|
| SO$_2$CH$_2$CH$_3$ | F | |
| SO$_2$CH$_2$CH$_3$ | Cl | |
| SO$_2$CH$_2$CH$_3$ | Br | m.p. 78-79° C. |
| CON(CH$_3$)$_2$ | F | |
| CON(CH$_3$)$_2$ | Br | |
| CON(CH$_2$CH$_3$)$_2$ | F | |
| CON(CH$_2$CH$_3$)$_2$ | Cl | |
| CON(CH$_2$CH$_3$)$_2$ | Br | |
| SO$_2$CH$_2$CH$_3$ | F | (HBr salt) |
| SO$_2$CH$_2$CH$_3$ | Cl | (HCl salt) |
| SO$_2$CH$_2$CH$_3$ | Br | (HBr salt) m.p. 196-198° C. |
| CON(CH$_3$)$_2$ | Br | (HBr salt) |

What is claimed:

1. A process for preparing a compound of the formula

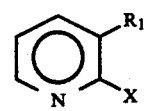

wherein
R$_1$ is C(O)R$_2$ or SO$_2$CH$_2$CH$_3$;
R$_2$ is C$_1$-C$_2$ dialkylamino; and
X is F, Cl or Br;
said process comprising reacting a compound of the Formula II with a compound of Formula III

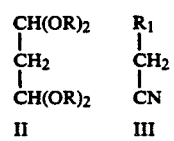

where $R_1$ is —$CH_3$ or —$CH_2CH_3$ and $R_1$ is as defined above in the presence of acetic anhydride, a $ZnX_2$ catalyst where X is as defined above at a temperature of 110°–150° C. to form a compound of the formula

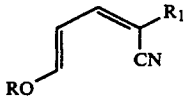   IV wherein $R_1$ and R are as defined above and reacting the compound of Formula IV with HX where X is as defined above in the presence of acetic acid at a temperature of 0°–60° C.

2. The process of claim 1 wherein $R_1$ is $C(O)R_2$ and $R_2$ is $C_1$ dialkylamino.

3. The process of claim 1 wherein $R_1$ is $SO_2CH_2CH_3$.

4. The process of claim 1 wherein X is Br.

5. The process of claim 1 wherein 3–6 moes of HX is used per mole of compound III and the reaction mixture stirred for 1–6 hours in order to form a crystalline salt of Compound I in the reaction mixture and separating the salt from the mixture.

6. A compound of Formula IV

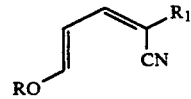

wherein

R is $CH_3$ or $C_2H_5$; and
$R_1$ is $C(O)R_2$ or $SO_2CH_2CH_3$; and
$R_2$ is $C_1$–$C_2$ dialkylamino.

7. A compound of claim 6 wherein $R_1$ is $C(O)R_2$.

8. The compounds of claim 6 wherein $R_1$ is $SO_2CH_2CH_3$.

9. A compound of Formula I

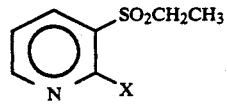   I wherein X is F, Cl or Br.

* * * * *